(12) United States Patent
Weyer et al.

(10) Patent No.: US 6,242,639 B1
(45) Date of Patent: Jun. 5, 2001

(54) PREPARATION OF NEOPENTYL GLYCOL HYDROXYPRIVALATE GRANULES

(75) Inventors: Hans-Jürgen Weyer, Bohenheim-Roxheim; Bernd Eck, Viernheim; Dieter Baumann, Frankenthal; Bernhard Maltry, Obrigheim, all of (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 08/925,795

(22) Filed: Sep. 9, 1997

(30) Foreign Application Priority Data

Sep. 13, 1996 (DE) ................................ 196 37 380

(51) Int. Cl.⁷ ...................................... B32B 5/16
(52) U.S. Cl. .......................... 560/179; 428/402; 560/189
(58) Field of Search ..................... 428/402; 427/212; 560/179, 189

(56) References Cited

U.S. PATENT DOCUMENTS

| | | | |
|---|---|---|---|
| 2,881,230 | 4/1959 | Buell | 260/674 |
| 4,665,219 | * 5/1987 | Merger et al. | 560/189 |
| 4,769,200 | 9/1988 | Hupfer et al. | 264/143 |
| 5,380,919 | * 1/1995 | Merger et al. | 560/179 |
| 5,936,115 | * 8/1999 | Melder et al. | 560/189 |

FOREIGN PATENT DOCUMENTS

| | | |
|---|---|---|
| 2183774 | 11/1995 | (CA) . |
| 3209747 | 3/1982 | (DE) . |
| 4445880 | 12/1994 | (DE) . |
| 210415 | 2/1987 | (EP) . |

* cited by examiner

*Primary Examiner*—H. Thi Le
(74) *Attorney, Agent, or Firm*—Keil & Weinkauf

(57) ABSTRACT

A method for preparing neopentyl glycol hydroxypivalate granules by application of a neopentyl glycol hydroxypivalate melt (1) onto a cooling belt (6) on which the melt solidifies, wherein the melt contains at least so 3 wt % of neopentyl glycol hydroxypivalate crystals, based on the total amount of neopenlyl glycol hydroxypivalate.

8 Claims, 2 Drawing Sheets

PREPARATION OF NEOPENTYL GLYCOL HYDROXYPRIVALATE GRANULES

FIELD OF THE INVENTION

The invention relates to a method for preparing neopentyl glycol hydroxypivalate granules, to the granules obtained and to the use of a granulating apparatus for preparing the granules.

BACKGROUND OF THE INVENTION

Neopentyl glycol hydroxypivalate (NHP) is used, inter alia, as a component of inside coatings of cans, in order to increase the impact strength of the inside coatings. Processing of NHP for subsequent use is usually carried out by an NTIP melt being ;applied to a cooling belt via a droplet former. Flat, flaky granules are formed in the process which tend to cake together when stored in packages and containers.

Said caking then impedes proportioning and removal of the granules from the packages and containers.

DE-A-35 22 359 discloses a process for the processing of crystalline, organic materials such as neopentyl glycol hydroxypivalate so as to result in a product which is more readily free-flowing. This involves a pulverulent material being compacted in a twin-shaft screw machine having corotating shafts or a molten material being crystallized and compacted, at bulk temperatures which are from about 1 to 20° C. below the melting point of the material used. The material is then expelled, through a heated perforated plate, into a zone having a lower pressure.

The perforated plate is heated to a temperature of from 1 to 30° C. above the melting point of the material, so that the individual crystals being passed past the wall of the perforated plate fuse to produce a film which, after it has solidified, forms a firm corset for the compacted crystalline material. In a downstream zone the extrudates are reduced in size and cooled. The flowability of the granules thus obtained is not adequate for all applications.

DE-C-32 09 747 discloses an apparatus for preparing granules from a melt, in which a two-phase mixture from a melt which contains crystal seeds is applied to a cooling belt by means of a rotor droplet former, hemispherical granules being obtained in the process.

SUMMARY OF THE INVENTION

It is an object of the present invention to provide a process for preparing NHP granules, which results in low-caking granules and which avoids the drawbacks of known processes.

This object is achieved according to the invention by a method for preparing neopentyl glycol hydroxypivalate granules by application of a neopentyl glycol hydroxypivalate melt onto a cooling area, preferably a cooling belt on which the melt solidifies, wherein the melt contains at least 3 wt % of neopentyl glycol hydroxypivalate crystals, based on the total amount of neopentyl glycol hydroxypiivalate.

Preferably the necpentyl glycol hydroxypivalate melt is applied to the cooling belt as a sheet-like layer and after solidification is subjected to size reduction to produce granules or the melt is applied dropwise.

The process according to the invention allows the preparation of NHP granules which exhibit no caking tendency in packages and containers, as the contact areas between individual granular, particles are small. The essentially spherical NHP granules in particular, which are obtained by dropwise application of the melt, are very low caking.

Prior to cooling, the melt preferably contains from 3 to 60 wt %, particularly preferably from 15 to 55 wt %, especially from 30 to 50 wt % NHP crystals, based on the total amount of NHP. The NHP crystals or NHP crystal nuclei may, in the process, be added to the melt as a solid. Advantageously they are generated in the NHP melt in a precrystallizer in which the melt is agitated mechanically and is cooled at the same time, the melt for this purpose preferably being cooled in a precooler to a temperature close to the melting point. For NHP this temperature is in the vicinity of 50° C. The throughput through the precooler and the precrystallizer can be adjusted so as to obtain the desired crystal content in the melt at the outlet of the precrystallizer. Preferably a portion of the melt leaving the precrystallizer is recycled into the precrystallizer, ie. fed back in between precooler and precrystallizer.

In so doing it is possible, by adjusting the return-flow ratio downstream of the precrystallizer and selecting a suitable throughput and temperature in the precrystal-lizer, to generate a desired proportion of crystals in the melt.

BRIEF DESCRIPTION OF THE DRAWINGS

The invention is explained below in more detail with reference to the drawing in which FIG. 1 shows an apparatus for preparing NHP granules in which

| | |
|---|---|
| 1 | is NHP melt, |
| 2 | is a precooler, |
| 3 | is a precrystallizer, |
| 4 | is a droplet former, |
| 6 | is a cooling belt. |

The apparatus is used for preparing guttate granules.

Figure 2:
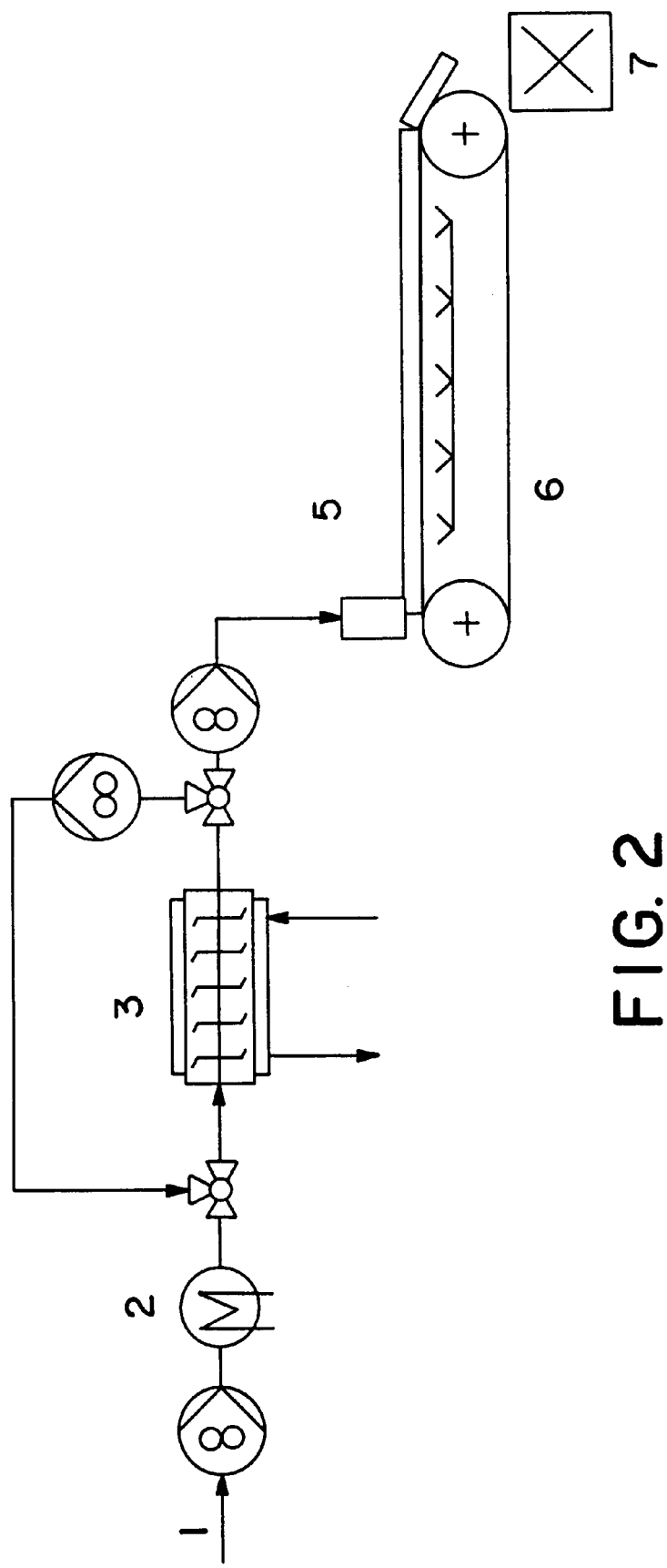

FIG. 2 shows an apparatus for preparing isometric or cuboid-like where

| | |
|---|---|
| 1 | is NHP melt, |
| 2 | is a precooler, |
| 3 | is a precrystallizer, |
| 5 | is an areal application system, |
| 6 | is a cooling belt, |
| 7 | is a crusher. |

The apparatuses used according to the invention are known per se. An apparatus comprising a droplet former is described, for example, in DE-C-32 09 747.

DETAILED DESCRIPTION OF THE INVENTION

Figure 1:
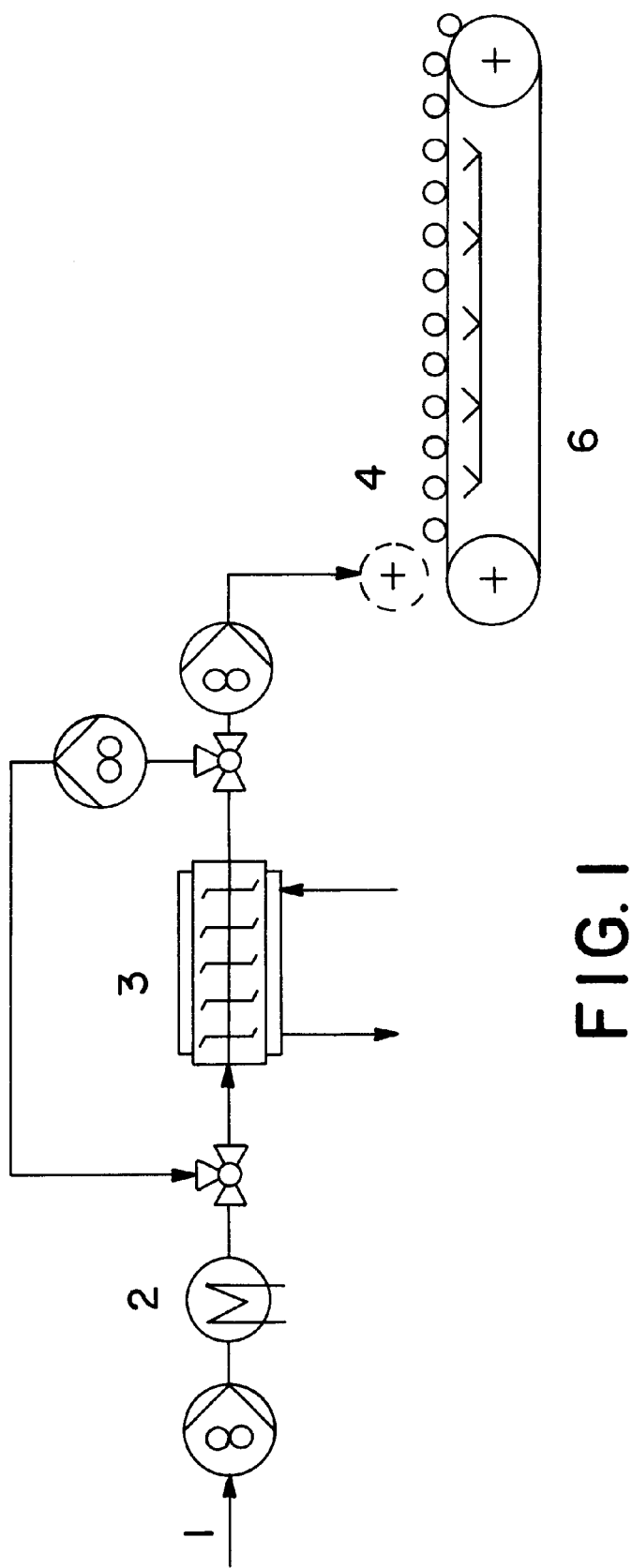

According to the embodiment shown in FIG. 1, the NHP melt (1) is initially passed through a precooler (2) and then through the precrystallizer (3), downstream of which a portion of the melt is shunted off and recycled into the precrystallizer (3). The remaining portion of the melt is applied, via a droplet former (4), to a continuously driven cooling belt (6) and solidifies thereon. The granular particles can be taken off at the end of the cooling belt. Owing to the high crystal content in the melt the latter has a high viscosity and solidifies rapidly. This allows the preparation of essentially spherical NHP granules which preferably have an average particle diameter of from 3 to 16, particularly preferably from 4 to 10, especially from 5 to 7 mm, the hot liquid NHP melt being cooled in the precooler (2) to a temperature close to the melting point (50° C.). Partial crystallization takes place in the downstream precrystallizer (3) by further heat removal from the melt. In the process, the desired crystal content in the melt is set via the magnitude of the amount of removed heat. The crystal slurry thus formed from crystals dispersed in the melt is a two-phase mixture. An increased degree of homogeneity is achieved by partial recycling of the crystal slurry to the inlet of the precrystallizer (3) by means of a pump. In so doing, the amount of the melt or slurry flowing through the precrystallizer is considerably larger than the amount conveyed toward the droplet former. The ratio of the crystal nuclei in the melt to be formed into drops with respect to the liquid constituents determines the shape of the drops and the solidification behavior of the drops on the cooling belt, the use of a melt having a high crystal content permitting the formation of spherical granule bodies. A suitable precrystallizer is described in DE-C-32 09 747.

To prepare the guttate NHP granules, the crystal melt or crystal slurry is conveyed to the droplet former by means of a pump, With the aid of the droplet former, the crystal-containing melt is dripped onto the cooling belt on which solidification of the drops takes place. A suitable droplet former is described, for example, in DE-C-32 09 747.

In a further embodiment of the invention, shown in FIG. 2, an areal application system (5) is used instead of the droplet former (4). The crystal-containing melt is prepared as in the process described previously. The areal application system (5) is designed so as to cause the melt to be spread over essentially the entire width of the cooling belt (6). To this end, the cooling belt may be provided with an edge delimitation, to achieve a uniform layer thickness over the entire width of the belt, The layer thickness of the sheet-like layer thus formed is preferably at least 15 mm, particularly preferably from 15 to 30 mm. Using the crystal-containing melt which rapidly solidifies on the cooling belt (6) allows the abovementioned high layer thicknesses to be achieved. At the end of the circulating belt the solidified layer breaks off, for example owing to gravity, and is further reduced in size in a crusher (7). This produces sheet-like granules having an average particle diameter of from 20 to 100 mm, preferably from 20 to 50 mm, in particular from 20 to 35 mm and at least 2 essentially parallel faces which are spaced at from preferably 15 to 30 mm. The shape of these NHP granules is preferably cuboidal or isometric. The resulting NHP granules exhibit a very low caking tendency.

The invention further relates to the use of a granulating apparatus for a melt, which comprises, successively connected via lines, a precooler (2), a precrystallizer (3), a droplet former (4) or an areal application system (5) for applying the melt to a downstream cooling belt (6) which, if an areal application system (5) is used, is followed by a crusher (7), for granulating neopentyl glycol hydroxypivalate.

The granules according to the invention have a higher bulk density and better proportionability than known granules. The essentially spherical granules, in particular, are readily proportionable and have a very high bulk density.

We claim:

1. A method for preparing neopentyl glycol hydroxypivalate granules which comprises i) generating neopentyl glycol hydroxypivalate crystals by passing a neopentyl glycol hydroxypivalate melt through a precrystallizer to obtain a melt which contains from 15 to 55 wt % of neopentyl glycol hydroxypivalate crystals, based on the total amount of neopentyl glycol hydroxypivalate, and ii) applying the melt from step i) to a cooling belt as a sheet-like layer, solidifying the melt and crushing the solidified melt to size reduction to produce granules, or iii) applying the melt from step i) dropwise onto a cooling belt and solidifying the drops.

2. A method as claimed in claim 1, wherein the neopentyl glycol hydroxypivalate melt is initially passed through a precooler and then through the precrystallizer, downstream of which a portion of the melt is shunted off and recycled into the precrystallizer and the remaining portion of the melt is applied, via a droplet former, to a continuously driven cooling belt and solidifies thereon.

3. A method as claimed in claim 1, wherein the neopentyl glycol hydroxypivalate melt is initially passed through a precooler and then through the precrystallizer, downstream of which a portion of the melt is shunted off and recycled into the precrystallizer and the remaining portion of the melt is applied, via an areal application system, to a continuously driven cooling belt, solidifies thereon and, having left the cooling belt is converted to granules in a crusher.

4. A method for preparing neopentyl glycol hydroxypivalate granules as claimed in claim 1, wherein the method comprises successively passing a neopentyl glycol hydroxypivalate melt through a precooler, a precrystallizer, and a droplet former for applying the melt to a downstream cooling belt, wherein the precooler, the precrystallizer, the droplet former and the cooling belt are connected via lines.

5. A method for preparing neopentyl glycol hydroxypivalate granules as claimed in claim 1, wherein the method comprises successively passing a neopentyl glycol hydroxypivalate melt through a precooler, a precrystallizer, an areal application system for applying the melt to a downstream cooling belt and a crusher, wherein the precooler, the precrystallizer, the areal application system, the cooling belt and the crusher are connected via lines.

6. Neopentyl glycol hydroxypivalate granules which can be prepared in accordance with a method as claimed in claim 1.

7. Neopentyl glycol hydroxypivalate granules as claimed in claim 6, which are essentially spherical neopentyl glycol hydroxypivalate granules having an average particle diameter of from 3 to 16 mm.

8. Neopentyl glycol hydroxypivalate granules as claimed in claim 6, having an average particle diameter of from 20 to 100 mm and at least two essentially parallel faces which are spaced at from 15 to 30 mm.

* * * * *

UNITED STATES PATENT AND TRADEMARK OFFICE
CERTIFICATE OF CORRECTION

PATENT NO. : 6,242,639 B1
DATED : June 5, 2001
INVENTOR(S) : Weyer et al.

It is certified that error appears in the above-identified patent and that said Letters Patent is hereby corrected as shown below:

Title page,
Item [54], the title should read: PREPARATION OF NEOPENTYL GLYCOL HYDROXYPIVALATE GRANULES Item [57], line 4 of the abstract, delete "so"; last line of the abstract, "neopenlyl" should be -- neopentyl --.

Signed and Sealed this

Thirteenth Day of November, 2001

Attest:

*Nicholas P. Godici*

NICHOLAS P. GODICI
*Attesting Officer*  *Acting Director of the United States Patent and Trademark Office*